United States Patent
Shi

(10) Patent No.: US 9,044,533 B2
(45) Date of Patent: Jun. 2, 2015

(54) METHOD FOR EMPTYING RECTUM

(75) Inventor: Huashan Shi, Jiangmen (CN)

(73) Assignee: Jiangmen Idear Hanyu Electrical Joint-Stock Co., Ltd., Jiangmen (CN)

( * ) Notice: Subject to any disclaimer, the term of this patent is extended or adjusted under 35 U.S.C. 154(b) by 571 days.

(21) Appl. No.: 13/077,326

(22) Filed: Mar. 31, 2011

(65) Prior Publication Data

US 2012/0150148 A1    Jun. 14, 2012

(30) Foreign Application Priority Data

Dec. 9, 2010  (CN) .......................... 2010 1 0580668

(51) Int. Cl.
  *A47K 3/022*  (2006.01)
  *A61M 3/06*  (2006.01)
  *A61M 3/02*  (2006.01)
  *E03D 9/08*  (2006.01)
(52) U.S. Cl.
  CPC ............... *A61M 3/06* (2013.01); *A61M 3/0225* (2013.01); *E03D 9/08* (2013.01)
(58) Field of Classification Search
  USPC ........ 4/443–448, 420.1–420.5; 604/275, 279, 604/514, 519
  See application file for complete search history.

(56) References Cited

U.S. PATENT DOCUMENTS

| 4,628,548 | A  | * | 12/1986 | Kurosawa et al. | ............. 4/420.4 |
| 4,761,837 | A  | * | 8/1988  | Takeda | ................................ 4/443 |
| 6,925,659 | B2 | * | 8/2005  | Sato et al. | ....................... 4/420.4 |
| 7,954,181 | B2 | * | 6/2011  | Lim | ................................... 4/420 |
| 2002/0042946 | A1 | * | 4/2002 | Jeon | ................................ 4/420.4 |

FOREIGN PATENT DOCUMENTS

| CN | 1341186 A | 3/2002 |
| CN | 1484724 A | 3/2004 |
| CN | 1997798 A | 7/2007 |

* cited by examiner

*Primary Examiner* — Lauren Crane
*Assistant Examiner* — Erin Deery
(74) *Attorney, Agent, or Firm* — Greer, Burns & Crain, Ltd.

(57) ABSTRACT

A method for emptying the rectum by using an electronic sanitary appliance arranged on a toilet, comprises: extending out a rectum flushing nozzle so that it locates underneath of the anus of a user who is seated on the toilet; spraying a first linear water flow to the anus from the rectum flushing nozzle, modifying the relative position between the rectum flushing nozzle and the user's anus so that the first linear water flow aims at the anus; spraying the anus with a second linear water flow from the rectum flushing nozzle to pass through the anus and into the rectum; spraying continuously the second linear water flow and stopping spray of the second linear water flow when the user has a desire to defecate, then the user discharges the substance in the rectum.

12 Claims, 11 Drawing Sheets

METHOD FOR EMPTYING RECTUM

CROSS-REFERENCE TO RELATED APPLICATIONS

This application is the U.S. National application which claims priority to Chinese Application 201010580668.X filed on Dec. 9, 2010, the disclosures of which are expressly incorporated herein.

FIELD OF THE INVENTION

The present invention relates to a method for spraying and rinsing the rectum, and more particularly to a method for emptying the rectum by spraying it with a water flow from an electronic sanitary appliance.

BACKGROUND OF THE PRESENT DISCLOSURE

In clinical practice, an enema is a common nursing process for treating constipation. It aims at assisting a patient in discharging excrement and accumulated gas. When the patient is subject to injection of an enema, it is required to insert a tube into the patient's rectum through his or her anus. This method has many drawbacks. Firstly, if a tube is inserted into a patient's rectum, especially when the patient suffers from hemorrhoids, he or she may feel pain in his or her anus. This causes the patient's suffering. Secondly, since the patient may fear injection of an enema into his or her rectum, his anal sphincter shrinks upon inserting a tube, and this is not favorable for insertion of the tube. Thirdly, in each process it is necessary to insert and extract the tube for injecting the enema, and to lubricate the front end of anal canal and surrounding of the patient's anus to relieve the pain, which involves a very extremely cumbersome and inconvenient procedure.

At present, several spray rinsing devices for cleaning human body have been developed. However, most of them are used for rinsing or washing the exterior of the human body, not for rinsing inside of the rectum.

For example, a water spraying device for cleaning a human body is disclosed in a Chinese patent application with publication number of CN1484724A. The spraying device comprises a vortex chamber and a water jetting body arranged in the vortex chamber, wherein the water jetting body includes a water spraying member and a chamber-housed member which is arranged in the vortex chamber and is tiltable. A water flow which flows in the vortex chamber generates a vortical flow around the chamber-housed member. A flow velocity difference generated by the vortical flow around the chamber-housed member involves oscillation of the water jetting body at an inclined position with respect to the vortex chamber. Such a water spraying device can not only clean a wider area of the human body and improve the reliability of water spraying, but also avoids use of a nozzle drive device, which reduces vibration and noise. However, such a water spraying device cannot perform cleaning on the deeper part of the human body like the rectum.

In addition, the patent application published under CN1341186A provides a human body cleaner. The nozzle head of the cleaner has a water swirling chamber which is located immediately below a nozzle opening and communicates with the nozzle opening via a small-diameter connection path. The water swirling chamber is formed as a hollow room having a tapered inner wall. A nozzle flow path for supplying flushing water to the water swirling chamber is eccentrically connected to the water swirling chamber, so that the water flowing through the nozzle flow path into the water swirling chamber swirls along the inner wall of the water swirling chamber and is sprayed from the nozzle opening in a spiral form or in an inverted truncated cone-shaped form. In this cleaner, it is possible to implement such a flushing manner that the two dimensional flushing range is not enlarged with the movement of the nozzle. Likewise, this cleaning means can't rinse inside of rectum and empty it.

Furthermore, CN1997798A discloses a multi-functional bidet, which is constructed in such a manner that an anus-cleansing function, a bidet cleansing function and an enema function are embodied in a single nozzle. The nozzle is projectably inserted into the lower central portion of the bidet body. It comprises an enema spray hole with a discharge hole arranged in it which has a diameter greatly or obviously less than that of the enema spray hole. In order to prevent turbulence of cleansing water after it passes through the discharge hole, a cleansing water guide rib is arranged in enema spray hole. In fact, it can't efficiently rinse the rectum or spray cleansing water into the rectum. However, this structure is difficult to manufacture.

Therefore, it can be seen that, up to now, no efficient method for rinsing inside of the rectum with a water flow have been developed

SUMMARY OF THE PRESENT INVENTION

The present invention is directed to provide a novel method for cleansing and emptying the rectum with an electronic sanitary appliance. This method utilizes a linear water flow which is sprayed into the rectum to a depth of 5 cm to 10 cm so that it can efficiently moisten and soften the dry and lumped excrement inside the rectum so as to break down it, this linear water flow can protect the anus from injury.

In one aspect, the present invention provides a method for cleansing and emptying the rectum by using an electronic sanitary appliance which is arranged on a toilet, the electronic sanitary appliance comprises a main body unit, a toilet seat, and a retractable human body flushing means which can extend out to locate underneath of the toilet seat and retract into the main body unit, and the human body flushing means comprises a nozzle head with an rectum flushing nozzle, the method comprises steps to be performed in the following sequence:

1) extending out the rectum flushing nozzle of the nozzle head so that it locates underneath of the anus of a user who is seated on the toilet seat;
2) spraying a first linear water flow to the anus from the rectum flushing nozzle and adjusting the relative position between the rectum flushing nozzle and the user's anus so that the first linear water flow aims at the anus;
3) spraying the anus with a second linear water flow for irrigating the rectum from the rectum flushing nozzle, so that the second linear water flow pass through the anus and enters into the rectum;
4) continuously spraying the second linear water flow and stopping spray of the second linear water flow when the user has a desire to defecate so that the user evacuates the substance in the rectum.

Preferably, the first linear water flow is sprayed under a relative pressure in the range from 0.03 MPa to 0.055 MPa, and the second linear water flow is sprayed under a relative pressure in the range from 0.07 MPa to 0.14 MPa.

Preferably, the second linear water flow is sprayed under a relative pressure which increases in a stepwise way.

The pressure difference between adjacent two relative pressures is in the range from 0.01 MPa to 0.06 MPa. Preferably, the pressure difference is in the range from 0.015 MPa to 0.025 MPa. More preferably, it is in range from 0.021 MPa to 0.022 MPa.

In step 4, after evacuating substance in the rectum, the user continues to sit on the toilet seat for a certain time and evacuates for at least one more time.

In step 4, after evacuating substance in the rectum, the user continues to sit on the toilet seat for at least 60 seconds, preferably 60-300 seconds, and more preferably 60-120 seconds.

The distance between the rectum flushing nozzle and the anus is in the range from 5 mm to 150 mm, and preferably from 40 mm to 50 mm. The outlet diameter of the rectum flushing nozzle is in the range from 0.8 mm to 2.5 mm. A ratio between the diameter and length of the nozzle hole is in the range of 1:3 to 1:20, and preferably 1:5 to 1:15.

The hole of the rectum flushing nozzle is in a truncated conical shape.

The vertex angle α of the hole in the truncated conical shape is larger than 0° and smaller than 15°, and preferably in a range from 3° to 10°.

The vertex angle α refers to an intersecting angle of any pair of extended lines in the wall of the truncated conical-shaped hole and in the same plane with the axis of the truncated conical-shaped hole.

The temperature of the first and the second linear water flow is in the range from 25° C. to 41° C. This temperature is preferably in the range from 35° C. to 38° C.

In an embodiment, the relative position between the rectum flushing nozzle and the user's anus is modified by moving back or forth the human body flushing means, or by moving back or forth his/her buttocks.

In another aspect, the present invention provides a method for emptying a rectum by using an electronic sanitary appliance which is arranged on a toilet, wherein the electronic sanitary appliance comprises a main body unit, a toilet seat, and a retractable human body flushing means which extends out to locate underneath of the toilet seat and retracts into the main body unit, and the human body flushing means comprises a nozzle head with an rectum flushing, nozzle, wherein the method comprises steps to be conducted in the following sequence:
 1) extending out the rectum flushing nozzle of the nozzle head so that it locates below the anus of a user sitting on the toilet seat;
 2) spraying the anus with a first linear water flow from the rectum flushing nozzle, adjusting the relative position between the rectum flushing nozzle and the user's anus so that the first linear water flow aims at the anus;
 3) spraying the anus with a second linear water flow for irrigating the rectum from the rectum flushing nozzle, so that the second linear water flow passes through the anus and enters into the rectum;
 4) spraying continuously the anus with the second linear water flow until the user has a desire to defecate, then spraying anus with the second linear water flow for a certain time and stopping the water flow so that the user evacuates substance in the rectum.

Wherein, the first linear water flow is sprayed under a relative pressure in the range from 0.03 MPa to 0.055 MPa, and the second linear water flow is sprayed under a relative pressure of the range from 0.07 MPa to 0.14 MPa.

Preferably, the second linear water flow is sprayed under a relative pressure which increases in a stepwise way.

The pressure difference between two adjacent relative pressures is in the range from 0.01 MPa to 0.06 MPa, and preferably in the range from 0.015 MPa to 0.025 MPa, and more preferably from 0.021 MPa to 0.022 MPa.

In step 4, after evacuating the substance in the rectum, the user sits on the toilet seat for a while and evacuates for at least one time.

In step 4, after evacuating the substance in the rectum, the user sits on the toilet seat for at least 60 seconds, preferably 60-300 seconds, and more preferably 60-120 seconds.

The distance between the rectum flushing nozzle and the anus is in the range from 5 mm to 150 mm, and preferably from 40 mm to 50 mm; the outlet diameter of the rectum flushing nozzle is in the range from 0.8 mm to 2.5 mm; and a ratio between the diameter and length of the nozzle hole is in the range of 1:3 to 1:20, and preferably 1:5 to 1:15.

Preferably, the hole of the rectum flushing nozzle is in a truncated conical shape.

The vertex angle α of the hole in the truncated conical shape is larger than 0° and smaller than 15°, and preferably from 3° to 10°.

The vertex angle α refers to an intersecting angle of any pair of extended lines in the wall of the truncated conical-shaped hole and in the same plane with the axis of the hole.

The temperature of the first and the second linear water flow is in the range from 25° C. to 41° C. This temperature is preferably in the range from 35° C. to 38° C.

The certain time in step 4) is at least 2 seconds, preferably at least 20 seconds, more preferably in the range from 30 seconds to 70 seconds.

The relative position between the rectum flushing nozzle and the user's anus is adjusted by moving back or forth the human body flushing means, or by moving back or forth his/her buttocks.

In another aspect, the present invention provides a method for emptying a rectum by using an electronic sanitary appliance which is arranged on a toilet, wherein the electronic sanitary appliance comprises a main body unit, a toilet seat, and a retractable human body flushing means which can extend out to underneath of the toilet seat and retracts into the main body unit, the human body flushing means comprises a nozzle head with an rectum flushing nozzle, wherein the method comprises steps to be conducted in the following sequence:
 1) extending out the rectum flushing nozzle of the nozzle head so that it locates underneath of the anus of an user who is seated on the toilet seat;
 2) spraying the anus with a linear flushing water flow for irrigating the rectum from the rectum flushing nozzle, adjusting the relative position between the rectum flushing nozzle and the user's anus so that the flushing water flow aims at the anus;
 3) spraying continuously the anus with flushing water flow so that the flushing water flow pass through the anus and enters into the rectum, then stopping the water flow when the user has a desire to defecate, so that the user evacuates substance in the rectum.

The flushing flow is sprayed under a relative pressure in the range from 0.03 MPa to 0.14 MPa. Preferably, it is in the range from 0.07 MPa to 0.14 MPa. The relative pressure increases in a stepwise way.

A pressure difference between adjacent two pressures which increase in a stepwise way is in the range from 0.01 MPa to 0.06 MPa, preferably in the range from 0.015 MPa to 0.025 MPa, and more preferably in the range from 0.021 MPa to 0.022 MPa.

In step 3, after evacuating substance in the rectum, the user sits on the toilet seat for a period of time and then evacuates for at least one more time.

The period of time is for at least 60 seconds, preferably 60-300 seconds, and more preferably 60-120 seconds.

The distance between the rectum flushing nozzle and the anus is in the range from 5 mm to 150 mm, and preferably from 40 mm to 50 mm; the outlet diameter of the rectum flushing nozzle is in the range from 0.8 mm to 2.5 mm; and a ratio between the diameter and length of the nozzle hole is in the range from 1:3 to 1:20, preferably 1:5 to 1:15.

The hole of the rectum flushing nozzle is in a truncated conical shape.

The vertex angle α of the hole in the truncated conical shape is larger than 0° and smaller than 15°, and preferably from 3° to 10°.

The vertex angle α refers to an intersecting angle of any pair of extended lines in the wall of the truncated conical-shaped hole and in the same plane with the axis of the hole.

The temperature of the flushing water flow is in the range from 25° C. to 41° C., preferably in the range from 35° C. to 38° C.

The relative position between the rectum flushing nozzle and the user's anus is modified by moving back or forth the human body flushing means, or by moving back or forth his/her buttocks.

In step 3, when the user has the desire to defecate, spraying the water flow for a certain time, and then stopping spraying the water flow so that the user discharges the contents of the rectum.

In particular, the certain time is at least 2 seconds, preferably at least 20 seconds, and more preferably in the range from 30 seconds to 70 seconds.

In one method according to the invention, a first linear water flow sprays under a relative water pressure which is low enough to relax the anus to aim at the anus, then a second linear water flow sprays under a higher relative water pressure which helps to completely relax the human anus or which is acceptable to the human, to pass through the anus and enter into the rectum. By increasing stepwisely or gradually the relative water pressure of the second linear water flow, the depth that the second linear water flow enters into the rectum increases gradually, so that the water flow efficiently sprays into the rectum to the depth of 5 cm to 10 cm.

In another method according to the invention, it is possible to directly spray a water flow of a higher relative pressure which is capable of entering into the rectum, without spraying a water flow under a lower relative pressure to aim at the anus, provided that the water flow under the higher relative water pressure sprayed directly can be accepted by the user. Besides, during the whole process, the water flow for irrigating the rectum can be sprayed under a constant relative water pressure.

The method according to the present invention can not only massage the acupuncture points around the anus and lubricate the intestinal canal, but also wet and soften the dry and agglomerated stool with the water flow gradually spraying into or perfusing the rectum so that one's bowels are open and he or she defecates easily. As a result, it is convenient and efficient to conduct defecation and rectum emptying. The anus rupture or the damage to the inner wall of the rectum caused by constipation or improper operation of conventional intubation enema can be avoided. In addition, since there is no adverse stimulation of water flow to the human body, injury to the anus or rupture of the fragile anal venous plexus can be avoided. Therefore, the present invention is especially suitable for the person suffering from senile constipation and hemorrhoids.

The method according to the present invention conveniently can be operated repetitively, and the rectum of a constipated person can be cleansed and emptied with comfortable feeling.

The method for emptying and flushing the rectum according to the present invention is suitable for daily defecation and expulsion of toxin from bowels. Harmful or bad substances produced due to accumulation of stool in the human body are prevented from being resorbed by the rectum. The method improves the state of health of the human body, eliminates internal toxin, and is also good for beauty care.

BRIEF DESCRIPTION OF THE DRAWINGS

FIG. 11 is a sectional view of the nozzle head along a longitudinal axis of the flushing means shown in FIG. 5a.

DETAILED DESCRIPTION

The embodiments of the present invention will be described in details hereinafter by reference to the accompanying drawings.

Figure 1:
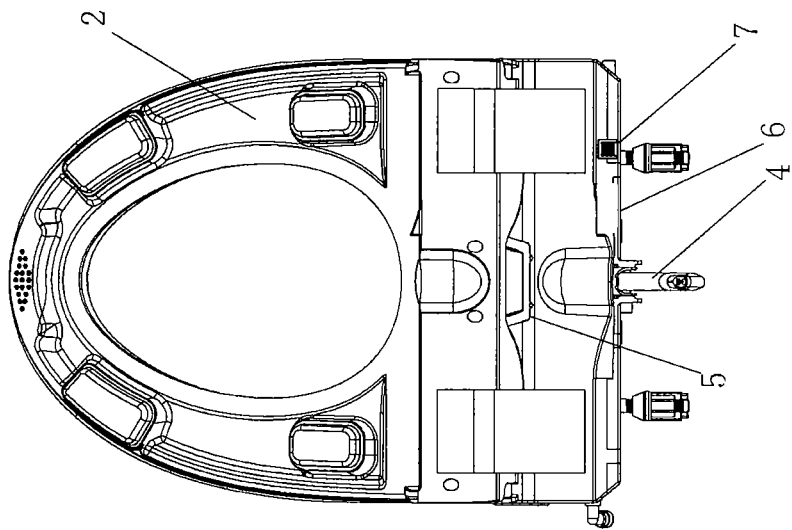
FIG. 1 is a front view of an electronic sanitary appliance according to the present invention.
Figure 2:
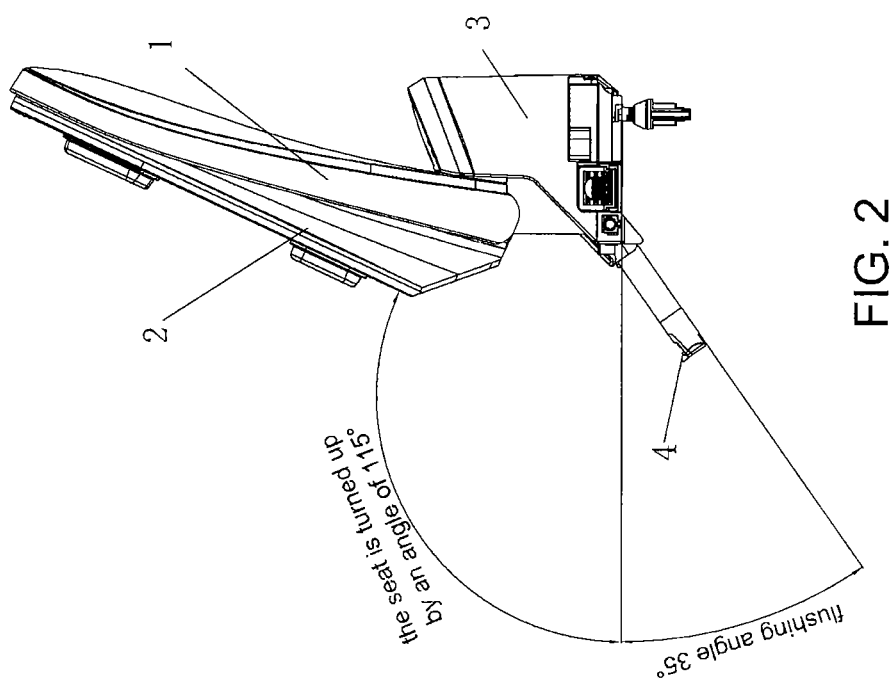
FIG. 2 is a side view of the electronic sanitary appliance according to the present invention.

As shown in FIGS. 1 and 2, the front view and the side view of an electronic sanitary appliance according to the present invention are illustrated, respectively. The electronic sanitary appliance according to the present invention comprises a main body unit 3 as well as a toilet seat 2 and a toilet cover 1 which are connected with a housing of the main body unit 3 by a hinge. The toilet seat 2 and the toilet cover 1 can be located at a horizontal position, and can also be turned up successively to a position at an angle of 115° with respect to the horizontal position.

Figure 3:
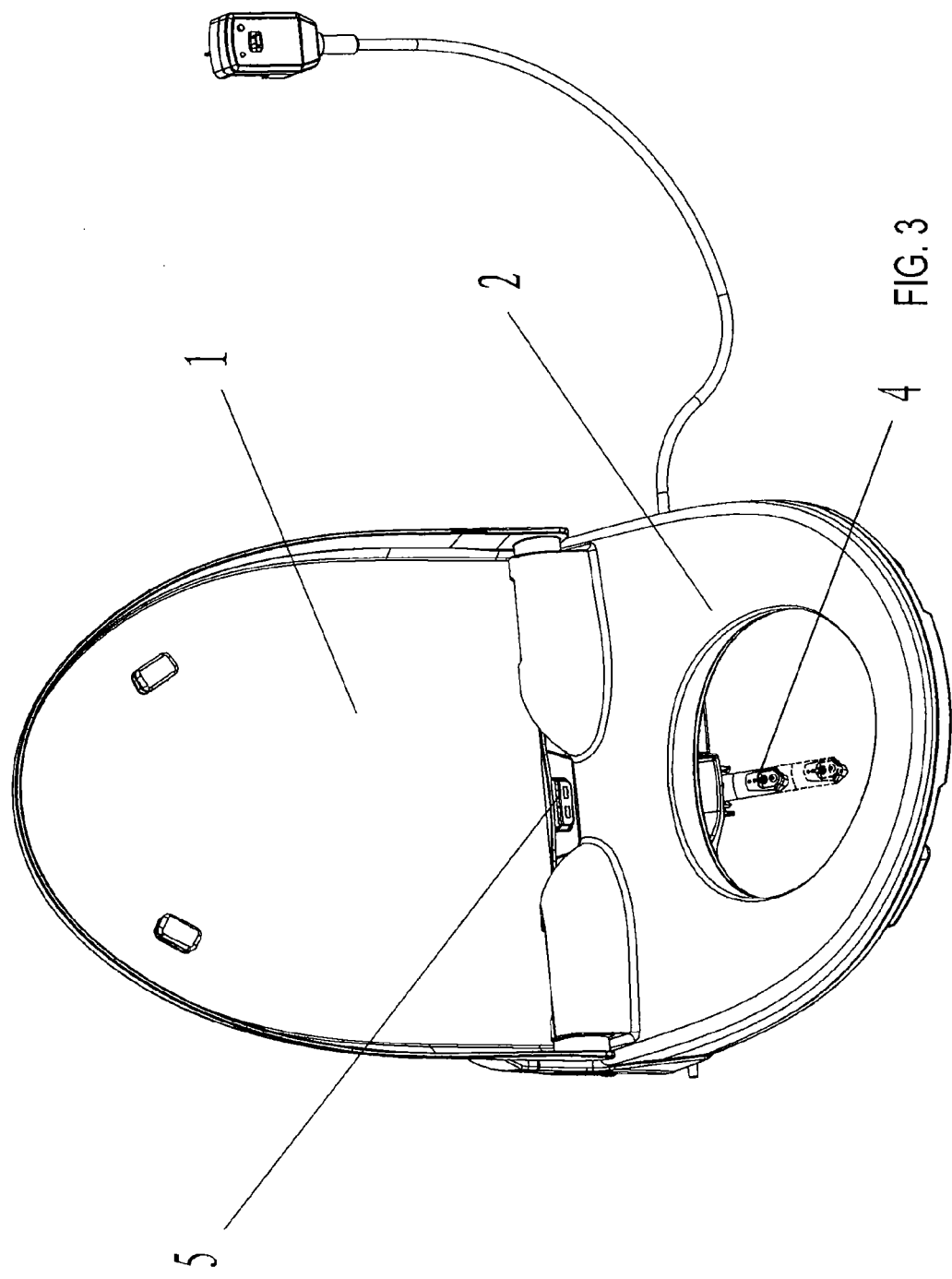
FIG. 3 is a perspective view of the electronic sanitary appliance in use according to the present invention.

Referring to FIGS. 1, 2 and 3, the electronic sanitary appliance further comprises a retractable flushing means 4 in tubular shape. As shown in FIG. 3, the flushing means 4 is mounted on a slide rail 44 which is arranged in the main body unit 3 and is tilted downward at an angle of 35° with respect to the horizontal direction, and can slide back and forth along the slide rail 44 when it is driven by a transmission mechanism (not illustrated), so that the flushing means 4 extends and retracts along the angle shown in FIG. 2. When the flushing means 4 is out of operation, it retracts into the main body unit 3. In operation, the flushing means 4 extends from the main body unit 3 along the angle (which is called a flushing angle) of 35° with respect to the horizontal direction, as shown in FIG. 2, so that the flushing water flow sprayed from the flushing means 4 along the direction that facilitates flushing.

As shown in FIG. 3, the flushing means 4 illustrated with solid lines extends to a middle position. The flushing means 4 shown in FIG. 4 and the flushing means 4 shown in FIG. 3 with dashed lines extend respectively to their maximum position.

Figure 5:
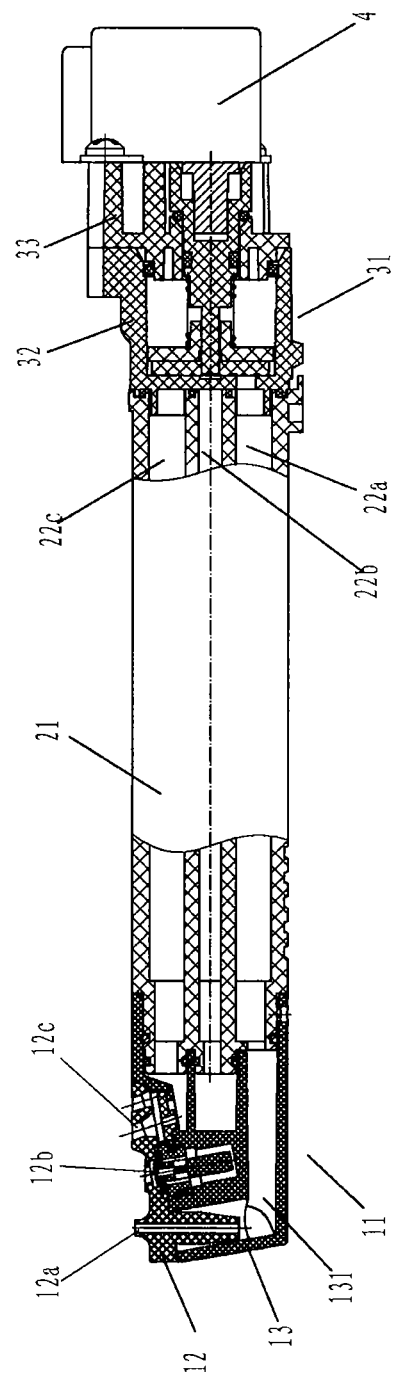
FIG. 5 is a sectional view of the flushing means of the electronic sanitary appliance according to the present invention, in which illustrates a sectional view for an rectum flushing nozzle 12a along a axis in the shape of a truncated cone.
Figure 6:
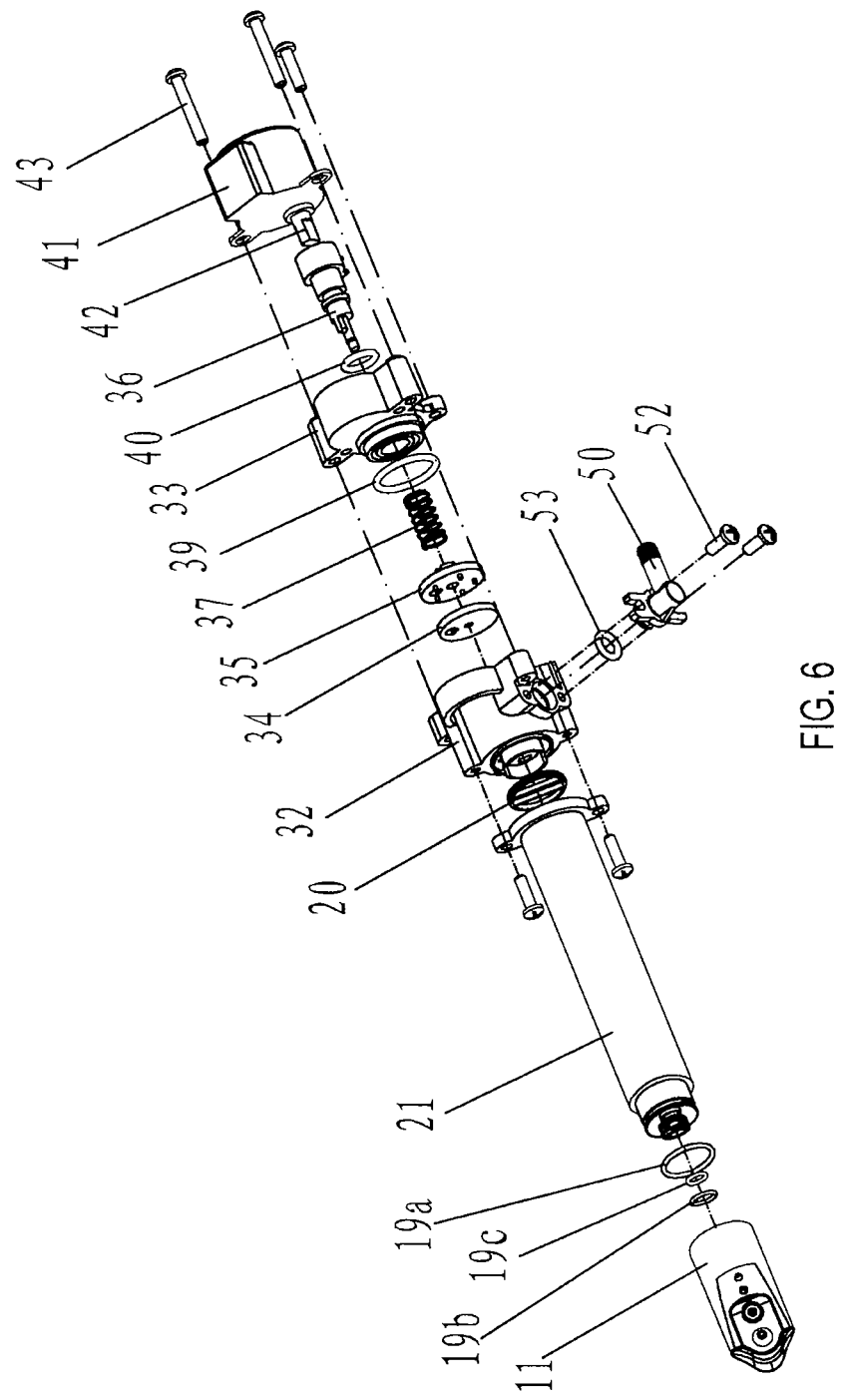
FIG. 6 is an exploded perspective view of the flushing means of the electronic sanitary appliance according to the present invention.

FIGS. 5 and 6 illustrate in detail the structure of the flushing means 4 of the present invention. FIG. 5 is a longitudinal sectional view of the flushing means 4. As shown in FIG. 5, the flushing means 4 of the present invention comprises a nozzle head 11, a spraying pipe 21, a valve 31 and a motor 41 which are connected successively in the axial direction. The nozzle head 11 is composed of a head base 13 and a head cover 12 being fastened onto the head base 13. On the head cover 12, three nozzles including a rectum flushing nozzle 12a, a buttock flushing nozzle 12b and a pubic area flushing nozzle 12c are arranged successively in the axial direction. In the head base 13, there are an enema water chamber 13a, a nozzle spindle accommodating chamber 13b, and a pubic area flushing nozzle accommodating chamber 13c which communicate respectively with the rectum flushing nozzle 12a, the buttock flushing nozzle 12b, and the pubic area flushing nozzle 12c. In the spraying pipe 21, there are three channels including a first channel 22a, a second channel 22b and a third channel 22c which extend in the axial direction and communicate with the enema water chamber 13a, the nozzle spindle accommodating chamber 13b, and the pubic area flushing nozzle accommodating chamber 13c respectively. The valve 31 is composed of a valve base 33 and a valve body 32 abuttingly joined thereto. The valve base 33 is fixed to the housing of the motor 41.

The toilet seat 2 is placed to its horizontal position on the toilet (not shown in FIG. 3). When a user sits on the toilet seat 2, the Infrared human inductive device 5 detects the user sitting on the toilet seat 2 so that the retractable flushing means 4 extends out from the main body unit 3 under the drive of a transmission mechanism which is controlled by an electric control device. The distance between the open mouth of the rectum flushing nozzle 12a and the user's anus can be is modified in the range from 5 mm to 150 mm. For example, the open mouth of the nozzle 12a is about 40 mm away from the anus. When the respect control means for spraying water flow is operated, the rectum flushing nozzle 12a and the buttock flushing nozzle 12b spray water flow towards the anus to perform enema cleaning, buttock flushing, and the pubic area flushing nozzle 12c sprays water flow towards the pubic area to perform pubic area flushing.

Figure 5A:
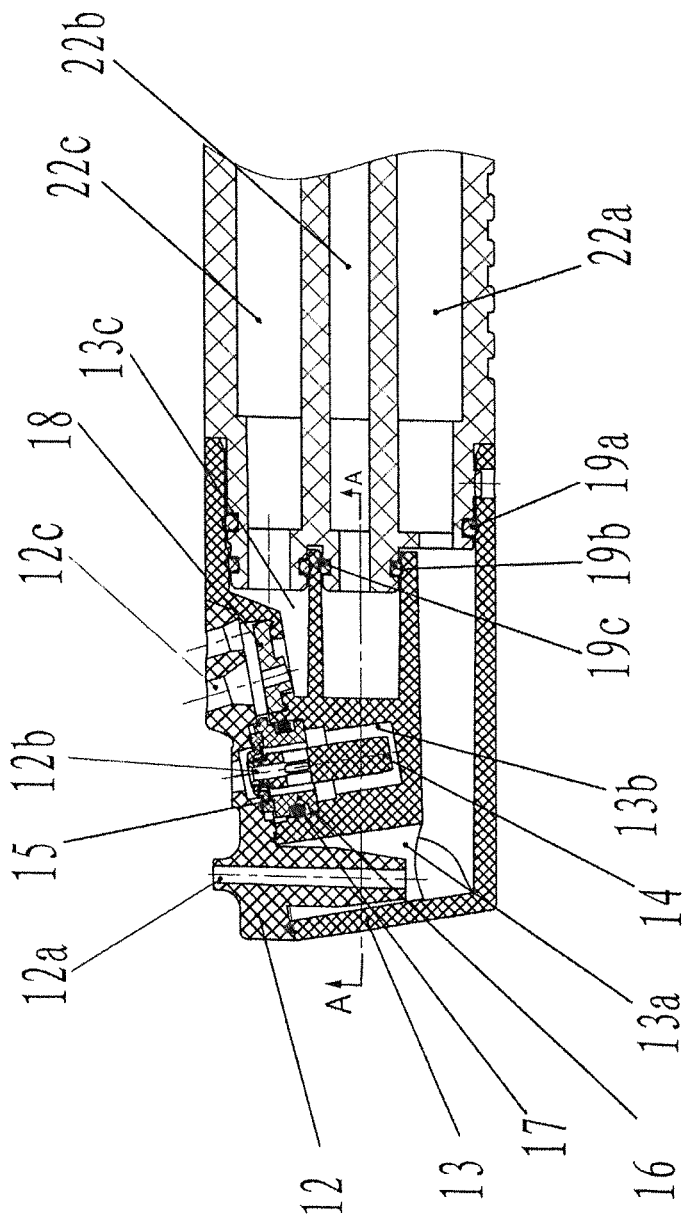
FIG. 5a is an enlarged sectional view of a nozzle head for the flushing means of the electronic sanitary appliance according to the present invention.
Figure 5B:
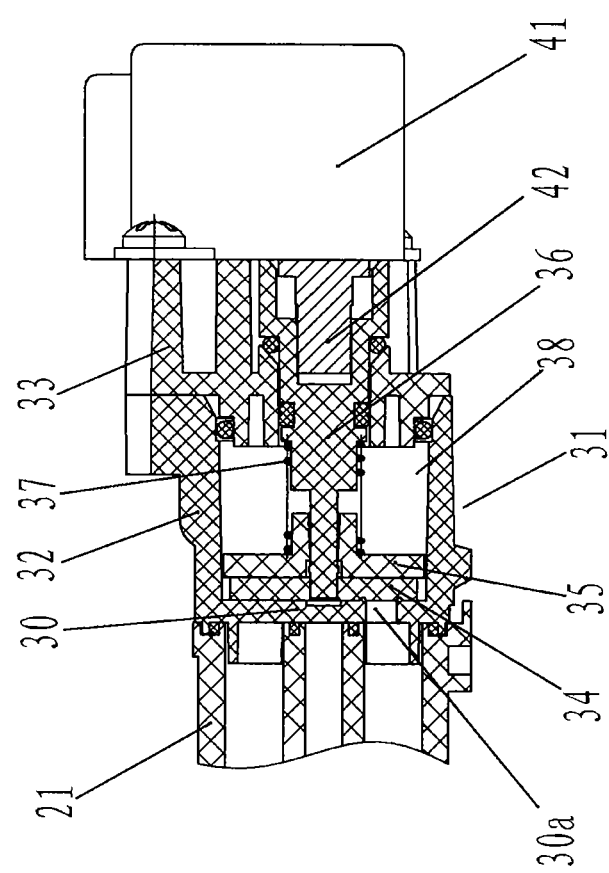
FIG. 5b is an enlarged sectional view of a valve in one state for the flushing means of the electronic sanitary appliance according to the present invention.

As shown in FIG. 5b, a valve chamber 38 is provided in the valve body 32. One end of the valve chamber 38 is closed by a spraying selection valve 30 and the other end combines with the valve base 33 and thereby is closed by it. In the valve chamber 38, there is a spraying selection shaft 36. One end the spraying selection shaft 36 is accommodated in an internal hole of the valve base 33 and is connected with the motor 41 by inserting the drive shaft 42 of the motor into the spraying selection shaft 36. The other end is successively fitted with a compression spring 37, a spraying selection plate 35 and a spraying selection cushion 34. A plurality of protrusions are arranged on the spraying selection plate 35 (as shown in FIG. 6), and notches corresponding to these protrusions are arranged on the spraying selection cushion 34. With the protrusions being inserted into the notches, the spraying selection plate 35 and the spraying selection cushion 34 are integrated with each other. Under spring action of the compression spring 37, the spraying selection plate 35 and the spraying selection cushion 34 are pressed to attach the spraying selection valve 30. The spraying selection plate 35 has a plate spraying selection hole 35a, see FIG. 5c, and the spraying selection cushion 34 has a cushion spraying selection hole 34a corresponding to the plate spraying selection hole 35a.

Figure 5C:
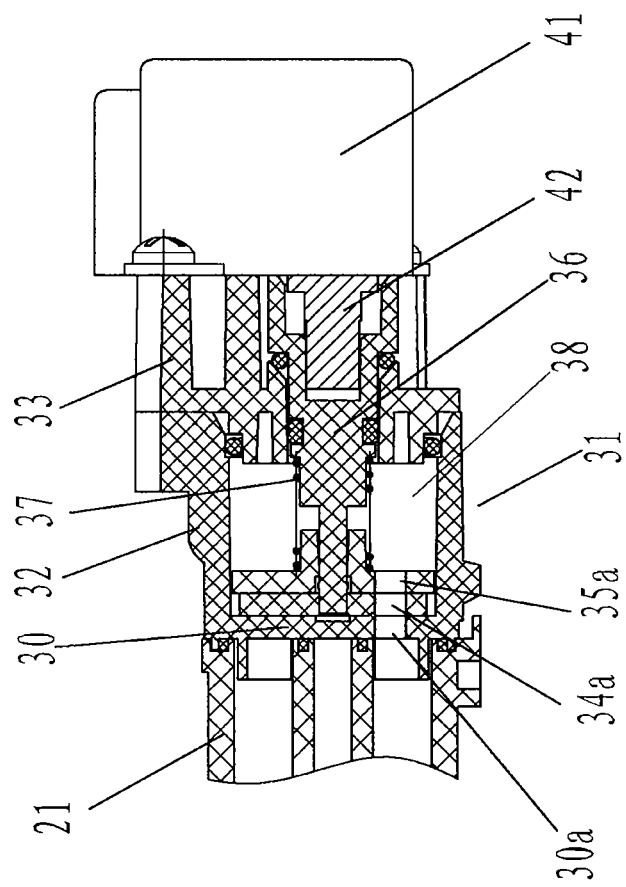
FIG. 5c is an enlarged sectional view of the valve in another state for the flushing means of the electronic sanitary appliance according to the present invention.
Figure 7:
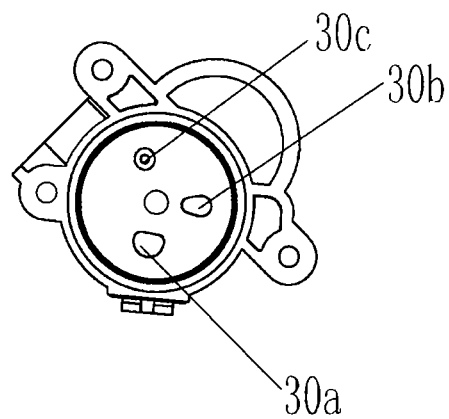
FIG. 7 is a front view of a spraying selection valve in the flushing means of the electronic sanitary appliance according to the present invention.

As shown in FIGS. 5b, 5c, and 7, the spraying selection valve 30 is provided with three holes including an enema valve hole 30a, a buttock flushing valve hole 30b, and a pubic area flushing valve hole 30c, wherein the pubic area flushing valve hole 30c is smaller than the enema valve hole 30a and the buttock flushing valve hole 30b. The enema valve hole 30a, the buttock flushing valve hole 30b, and the pubic area flushing valve hole 30c communicate respectively with the first to third channels 22a-22c. The plate spraying selection hole 35a can communicate with one of valve hole 30a, 30b and 30c.

Since the spraying selection cushion 34 is arranged between the spraying selection plate 35 and the spraying selection valve 30, a seal is formed there between under the pressure of the compression spring 37. When the plate spraying selection hole 35a communicates with one of the valve holes 30a, 30b and 30c, the spraying selection cushion 34 prevents water in the valve chamber 38 from leaking through other two valve holes. For example, as shown in FIG. 5c, when the plate spraying selection hole 35a communicates with the enema valve hole 30a, water in the valve chamber 38 flows in the first channel 22a through the plate spraying selection hole 35a and the enema valve hole 30a. Due to sealing effect of the spraying selection cushion 34, water in the valve chamber 38 is prevented from leaking to the second and third channels 22b, 22c through the buttock flushing valve hole 30b and the pubic area flushing valve hole 30c.

In addition, the spraying selection cushion 34 is integrated with the spraying selection plate 35 and the valve chamber 38 is sealed by bringing the compression spring 37 into close or tight contact with the valve 30. During operation, water supply to the first to third channels 22a, 22b, and 22c can be realized respectively, by a plate spraying selection hole 35a arranged on the spraying selection plate 35 which communicates with one of the valve holes 30a, 30b and 30c. Therefore, during assembling, it is not necessary to bring the outer circumferential surface of the spraying selection plate 35 into close contact with the inner surface of the valve chamber 38 to guarantee sealing of the valve chamber 38. This simplifies assembly.

Figure 4:
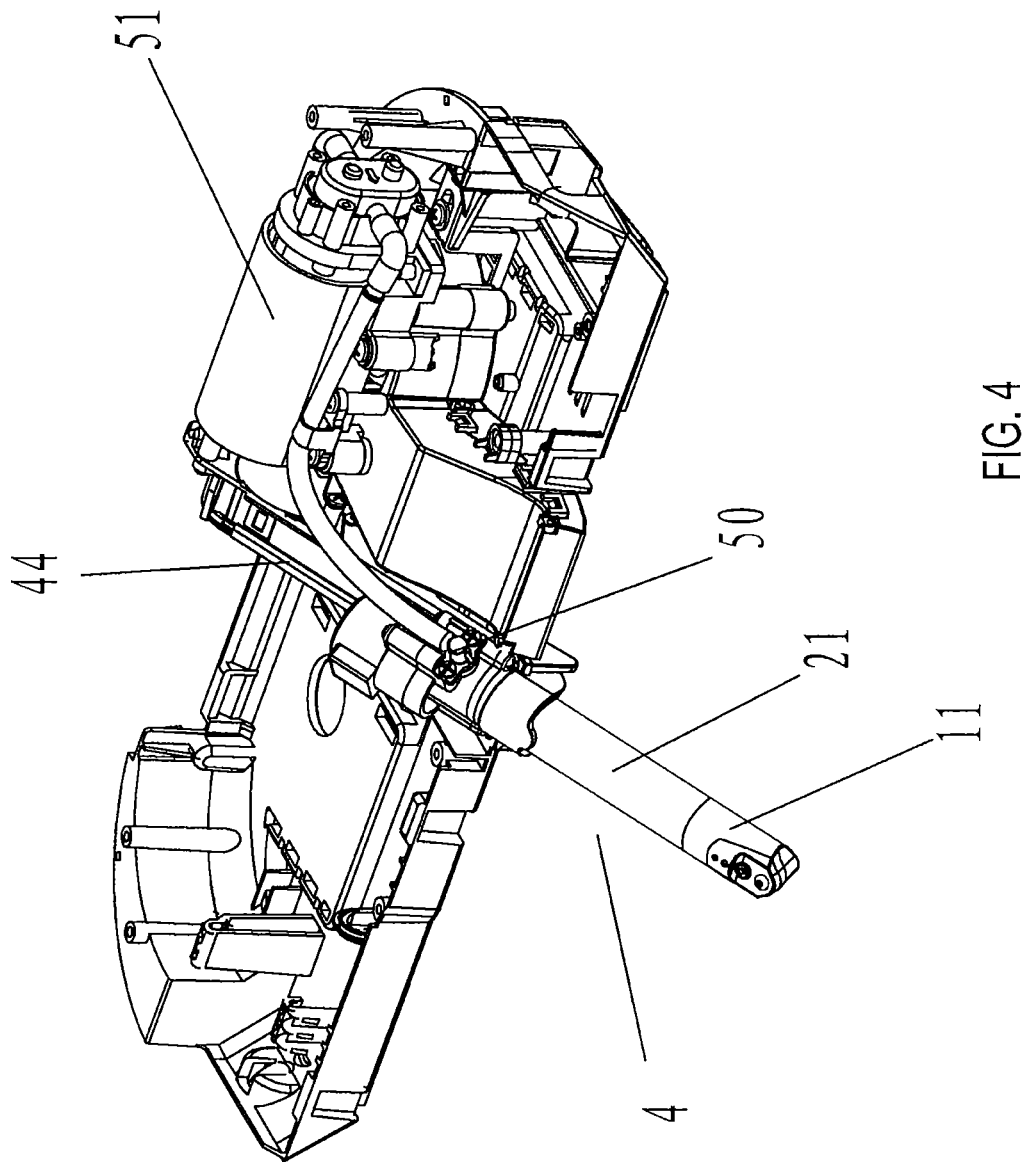
FIG. 4 is a perspective view of a flushing means of the electronic sanitary appliance in an installment state according to the present invention.

As shown in FIG. 6, the valve chamber 38 is provided with an opening in its side, and a spraying pipe joint 50 is fastened into the opening with a screw 52 so that the valve chamber 38 communicates with a water pump 51 through the spraying pipe joint 50 (see FIG. 4). A water heating tank, not shown in the figure, can be arranged in the main body unit 3 at a side opposite to the water pump 51. In other words, the water heating tank and the water pump 51 are arranged on two sides of the flushing means 4 in the main body unit 3. The water heating tank is connected with a water source, such as tap-water, through a valve.

In the present invention, the toilet seat 2 and/or the toilet cover 1 can be utilized as a water tank. As shown in FIGS. 2 and 4, each of the toilet seat 2 and the toilet cover 1 has an internal hollow chamber. By communicating the internal hollow chamber with the water heating tank (in which an electric heater is provided) in the main body unit, it is possible to increase the effective volume of the water tank for storing warm water. Generally, it is possible to increase the volume of the water tank to 1.2 liters or more, so that continuous or adequate supply of warm water can be guaranteed when an enema action is conducted. For example, only the toilet seat 2 is utilized as the water tank, one end of the toilet seat 2 communicates with the water heating tank, and the other end communicates with the water pump 51. During an enema operation, the electric heater in the water heating tank is turned on, and the water pump 51 is started. The warm water which has been heated in the water heating tank flows through the toilet seat 2 and is pumped into the valve chamber 38 by the water pump 51 to supply flushing water. If both the toilet seat 2 and the toilet cover 1 are utilized as the water tank, it is possible to connect one end of the toilet seat 2 and that of the toilet cover 1 with the water heating tank simultaneously, and the other ends of the toilet seat 2 and the toilet cover 1 with the water pump 51.

The electric heater in the water heating tank heats the water to a temperature in the range of 25° C. to 41° C., preferably in the range of 35° C. to 38° C., which is consistent with the human body temperature. Hence, enema cleansing with warm water in this temperature helps the user to relax his or her anus so as to rinse the rectum which prevents the user from being irritated by a cool water flow with a lower temperature.

Further referring to FIGS. 5a and 6, the structure of the nozzle head is described in details. On the head cover 12, there are the rectum flushing nozzle 12a, the buttock flushing nozzle 12b and the pubic area flushing nozzle 12c. In the head base 13, there are the enema water chamber 13a, the nozzle spindle accommodating chamber 13b and the pubic area flushing nozzle accommodating chamber 13c for accommodating respective nozzles.

Figure 8:
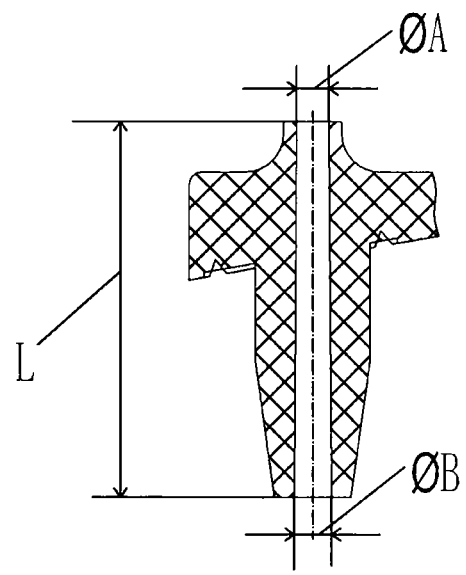
FIG. 8 is an enlarged sectional view of the rectum flushing nozzle 12a according to the present invention.
Figure 9:
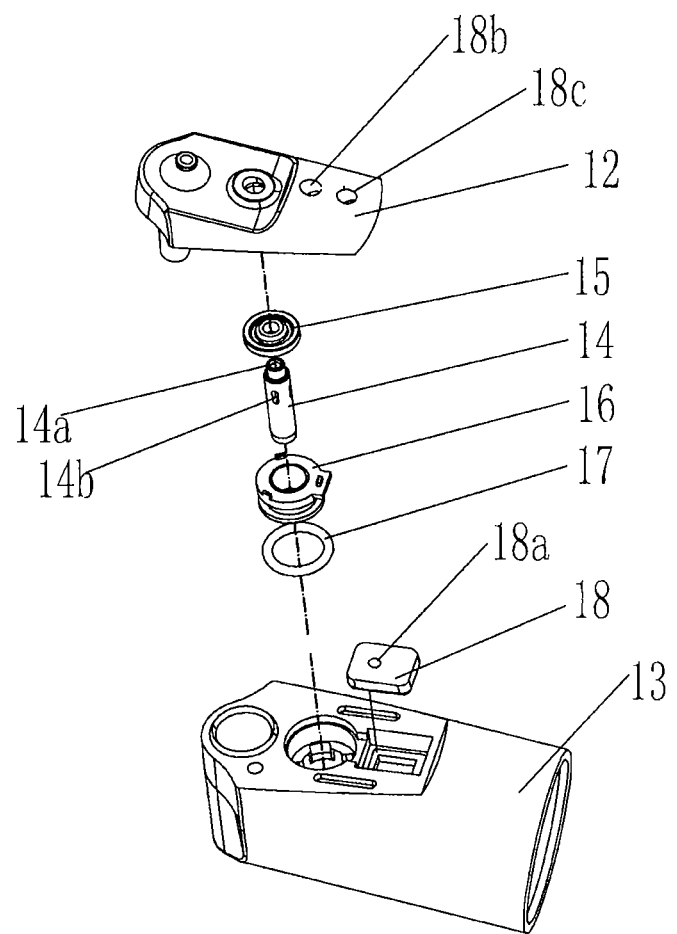
FIG. 9 is an exploded view of the nozzle head according to the present invention.

The structure of the rectum flushing nozzle 12a is described below. Since it is required that during enema action the water flow sprayed from the rectum flushing nozzle 12a should enter into the rectum for a distance in the range from 5 cm to 10 cm, the sprayed water flow should be converged to a line, i.e., developed into a linear water column. The hole of the nozzle 12a shown in FIG. 5 is of a slightly truncated conical shape, so that the inlet diameter is slightly larger than the outlet diameter. For example, see FIG. 8, the outlet diameter $\phi A$ is 1.3 mm, the inlet diameter $\phi B$ is 1.5 mm, and the length L is 14.7 mm. When water is supplied to the nozzle 12a at a pressure in the range from 0.07 MPa to 0.12 MPa, the linear water column from the nozzle 12a can spray into the rectum for a distance in the range from 5 cm to 10 cm.

Therefore, in order to realize a linear water column spray from the nozzle 12a, the vertex angle $\alpha$ of the truncated conical-shaped hole of the nozzle 12a should be larger than 0° and smaller than 15°, and preferably in the range from 3° to 10°. Referring to the sectional view in FIGS. 5a and 8, the vertex angle $\alpha$ of a truncated cone refers to an intersecting angle of the extended lines in a wall of the truncated conical hole as indicated in the figures. As shown in this figures, the outlet diameter $\phi A$ of the truncated conical-shaped hole is in the range from 0.8 mm to 2.5 mm, preferably from 1.2 mm to 1.4 mm, and the ratio $\phi A:L$ between the outlet diameter $\phi A$ and the hole length L is 1:3 to 1:20, preferably 1:5 to 1:15. In this way, the inlet diameter $\phi B$ is slight longer than the outlet diameter $\phi A$.

The axis of the nozzle 12a is substantially perpendicular to that of the nozzle head 11.

To facilitate fabrication and prevent turbulent flow, the enema water chamber 13a runs through along axial or longitudinal direction of the nozzle head 11. The term "run through" means that cross-section size of the enema water chamber 13a is substantially constant, or the whole enema water chamber 13a slightly and evenly tapers in the axial direction, and no discharge hole with a cross-section size greater or obviously less than that of the enema water chamber 13a is provided in the enema water chamber 13a. As shown in FIG. 5, cross-section size of one longitudinal outlet end 131 of the enema water chamber 13a is substantially equal to that of the other longitudinal inlet end of the chamber 13a. As shown in FIG. 5a, the cross section size or diameter of the rectum flushing nozzle 12a is substantially smaller than that of the chamber 13a.

Figure 10:
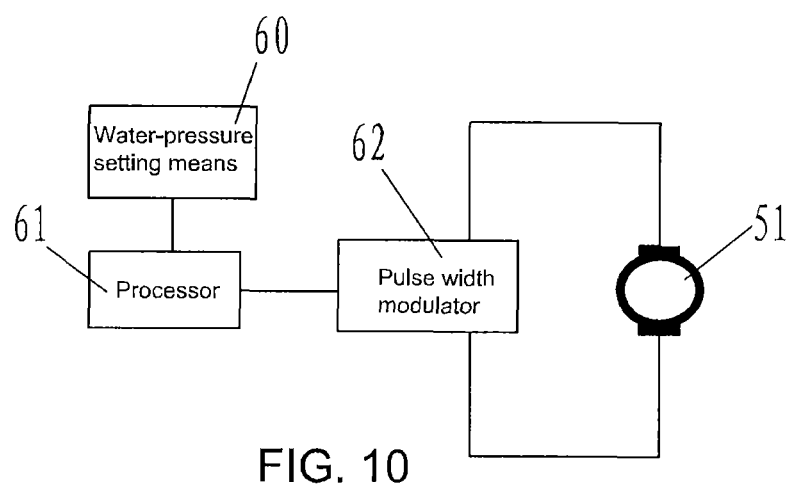
FIG. 10 is a diagram showing the principle of water-pressure regulation for the rectum flushing nozzle of the electronic sanitary appliance according to the present invention.
Figure 11:
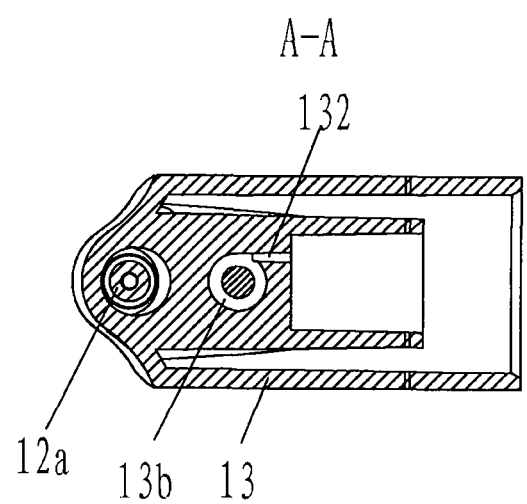

FIG. 10 shows an essential component of a water-pressure regulator for the rectum flushing nozzle of the electronic sanitary appliance according to the present invention. According to the present invention, the water-pressure regulation for the rectum flushing nozzle is realized by regulating the power supply for the water pump 51 which is output from the pulse width modulator 62. The water pressure value of the rectum flushing nozzle for the electronic sanitary appliance is set by the user with a water-pressure setting means 60. A processor 61 receives a value of water pressure being set by the water-pressure setting means 60, and converts it into a pulse width modulation parameter which is sent to the pulse width modulator 62. Then, with the pulse width modulation parameter, the pulse width modulator 62 changes the pulse width of the pulse power supply which is the supply for the water pump 51. In this way, it realizes the water-pressure regulation of the rectum flushing nozzle for the electronic sanitary appliance.

The water-pressure setting means 60 can be a local means or a remote means.

The operating procedure of the method according to the present invention will be described in details hereinafter by reference to the accompanying drawings.

Firstly, the user sits on the toilet seat 2, the flushing means 4 extends out from the main body unit 3 to underneath of the toilet seat 2, and the rectum flushing nozzle 12a of the nozzle head 11 is moved below the anus to face towards the anus.

Then, the relative outlet water-pressure of the rectum flushing nozzle 12a is controlled in the range from 0.03 MPa to 0.05 MPa by the water-pressure setting means 60, so that the first linear water flow sprayed from the nozzle 12a under this water-pressure can be used to aim at the anus. The relative outlet water-pressure generally refers to the relative water-pressure in the enema water chamber 13a. When the spraying selection valve 30 is opened, water is supplied to the rectum flushing nozzle 12a by the water pump 51 so that the nozzle 12a sprays continuously a linear water flow to the user's anus. At this time, the flushing means 4 is controlled to move back or forth, or the user himself moves his/her buttocks, so that the first linear water flow sprayed from the nozzle 12a aims at the anus.

The relative water-pressure in the context of the present invention refers to a water-pressure which is calculated or obtained by taking the atmospheric pressure as a starting point. In other words, the relative water-pressure refers to the absolute water-pressure in the enema water chamber 13a minus the atmospheric pressure.

Then, the outlet relative water-pressure can be increased to the range from 0.07 MPa to 0.14 MPa by the water-pressure setting means 60 so that the second linear water flow under this outlet pressure sprays to, the anus and enters the rectum. Generally, the second linear water flow sprays under an outlet water-pressure which is increased stepwisely, and each increasing degree of the outlet relative pressure is controlled in the range from 0.01 MPa to 0.06 MPa.

The second linear water flow sprays continuously to the anus and enters into the rectum until the user has desire to defecate. After that, the second linear water flow sprays for another several seconds (generally in the range from 30 seconds to 70 seconds). When the user cannot tighten the anus and cannot help defecating, the spraying selection valve 30 is controlled to close so that the nozzle 12a stops spraying water and the transmission mechanism drives the retractable flushing means 4 to move back into the main body unit 3. Then the user evacuates the matter in the rectum quickly.

After the user defecates, since there is still some substance in the rectum, it is required for the user to continue to sit on the toilet seat for a while, generally for 60 to 120 seconds, in order to defecate several times. The user may not stand up until his desire to defecate disappears.

The relative pressure of outlet water for emptying the rectum is controlled in the range from 0.07 MPa to 0.14 MPa to prevent anus from suffering by a water flow spray under an excessive pressure.

Generally, for a user with regular bowel movement, during the routine process for emptying the rectum, the pressure for the linear-water flow spraying into the rectum, namely, the relative pressure of outlet water for an enema action is in the range from 0.07 MPa to 0.118 MPa. Thus, pressure of the water flow should be increased from 0.07 MPa stepwisely to 0.118 MPa. For example, the outlet pressure can be set successively to three pressures of 0.07 MPa, 0.096 MPa, and 0.118 MPa, so that the relative pressure of outlet water is increased stepwise from a low value to a high value.

For some users, it is possible that the enema action can be realized by setting the relative pressure of outlet water in the range from 0.07 MPa to 0.08 MPa. For example, the relative pressure of outlet water is directly set at 0.075 MPa to empty the rectum.

If the user is a patient suffering from severe constipation, during the process for emptying the rectum, it is required to spray into the rectum a cleansing water flow under a higher relative pressure, generally up to 0.14 MPa. Therefore, for such a user, relative pressure of the water flow can be increased from 0.07 MPa stepwisely to 0.14 MPa. For example, pressure of the water flow can be set successively to four levels of 0.07 MPa, 0.096 MPa, 0.118 MPa, and 0.14 MPa, so that it is increased stepwise for conducting the enema action.

Embodiment 1

The outlet diameter of the rectum flushing nozzle 12a of the electronic sanitary appliance is 1.3 mm.

Firstly, the electronic sanitary appliance is switched on and the main body unit 3 is started. The water in the water heating tank is heated by an internal heater until its temperature reaches 37° C.

The user sits on the toilet seat 2 which is arranged on a toilet. The rectum flushing nozzle 12a of the nozzle head 11 extends out to locate beneath the user's anus. The distance between the rectum flushing nozzle 12a and the user's anus is about 40 mm.

After the relative pressure of outlet water of the rectum flushing nozzle 12a is set to 0.04 MPa by the water-pressure setting means 60, the spraying selection valve 30 is opened and the water pump 51 is started to supply water. The water pressure in the enema water chamber 13a, namely the relative pressure of outlet water of the rectum flushing nozzle 12a reaches 0.04 MPa, and a linear water flow sprays to the user's anus from the rectum flushing nozzle 12a. The flushing means 4 is controlled to extend out and move back or forth, or the user moves back or forth his/her buttocks, so that the linear water flow spray from the nozzle 12a aims at the anus.

Then, the water-pressure setting means 60 adjusts the relative pressure of outlet water to increase, so that the water flow sprays from the nozzle 12a under the pressure of 0.05 MPa. At this time, the linear water flow brings the user's anus into a critical state, namely, the anus is subject to the same pressure at its both sides and is relaxed. In other words, the anus is in a marginal state from closing to opening.

When the user feels that the anus is completely relaxed, he/she may increase the relative pressure by operating the water-pressure setting means 60, so that the pressure of outlet water reaches 0.075 MPa. The linear water flow spraying under this pressure is capable of passing through the user's anus and enters into the rectum.

The linear water flow being sprayed under 0.075 MPa continuously enters into the user's rectum until the user has a desire to defecate. Then the linear water flow sprays for 30 seconds more and the water pump 51 is stopped so that the rectum flushing nozzle 12a stops spraying. At the same time, the transmission mechanism drives the retractable flushing means 4 to retract into the main body unit 3, and the user quickly defecates the substance in the rectum.

In case that the relative pressure of outlet water reaches 0.075 MPa and the user feels that he/she can accept the linear water flow sprayed under a higher relative pressure, the relative pressure of outlet water flow can be successively increased to 0.096 MPa and 0.118 MPa so that the linear water flow sprays into the rectum more efficiently. The linear water flow sprays continuously until the user has a desire to defecate, then the linear water flow sprays for 30 seconds more before the user defecates. Alternatively, the relative pressure of the water flow can be successively increased to 0.096 MPa, 0.118 MPa, and 0.14 MPa, so that the linear water flow sprays into the rectum until the user has a desire to defecate, and then the linear water flow sprays for 30 seconds more before the user defecates.

In other words, in case that when the user is subject to the flushing action with a linear water flow under a relative pressure of 0.075 MPa, the user feels that he/she can bear a water flow sprayed under a slightly higher relative pressure, the relative pressure for spraying the linear water flow can be increased to 0.096 MPa by the water-pressure setting means 60 to perform the rectum flushing. In case that when the user is subject to a water flow spraying under a pressure of 0.096 MPa, he/she feels that he/she can bear a water flow spraying under a higher relative pressure, the pressure can be further increased to 0.118 MPa by the water-pressure setting means 60 to perform the rectum flushing. In case that when the user is subject to a water flow spraying under a pressure of 0.118 MPa, he/she feels that he/she can bear a water flow spraying under a higher pressure, the pressure can be increased to 0.14 MPa by the water-pressure setting means 60 to perform the rectum flushing. At any pressure of the outlet water described above, when the user has a strong desire to defecating, it is preferred for the user to be subject to the water flow waiting for at least 30 seconds more before he defecates.

It should be noted that the relative pressure of outlet water is regulated by increasing with a stepwise pressure difference in the range from 0.01 MPa to 0.06 MPa.

After the user defecates, he/she preferably remains seated on the toilet for 60-120 seconds more, and defecates several times before he/she stands up. In this way, a process for emptying the rectum is completed.

For the user suffering from severe constipation, during defecation the above process may be repeated several times e.g. three to five times, in order to realize a better emptying effect.

Furthermore, the user can also select only one relative pressure of outlet water that he/she can bear, for example, 0.118 MPa or 0.14 MPa, and the water flow is sprayed under this pressure throughout the above process including the process for aiming at the anus and for conducting the enema action.

Embodiment 2

The outlet diameter of the rectum flushing nozzle 12a is 0.8 mm.

With the temperature of the water flow controlled at 38° C., the user is seated on the toilet seat 2, and the rectum flushing nozzle 12a of the nozzle head 11 is located beneath the user's anus. The distance between the rectum flushing nozzle 12a and the user's anus is 5 mm.

The relative pressure is set to 0.03 MPa by the water-pressure setting means 60. The water pump 51 is started for supplying water, and a linear water flow is sprayed to the user's anus by the rectum flushing nozzle 12a. The flushing means 4 is controlled to extend out and then move back or forth so that the linear water flow sprayed from the nozzle 12a aims at the anus.

The water pressure is regulated to reach 0.05 MPa, so that a linear water flow is sprayed to the user which brings his/her anus into a critical state.

Then, the relative pressure can be increased successively to 0.075 MPa, 0.096 MPa, 0.118 MPa, and 0.14 MPa, so that the linear water flow is capable of pass through the user's anus and enters into the rectum. The water flow is sprayed continuously under the water pressure of 0.14 MPa for a certain time till the user has a desire to defecate. Then the rectum flushing nozzle 12a stops spraying and the transmission mechanism drives the retractable flushing means 4 to retract into the main body unit 3. After that the user quickly defecates or discharges the substance in the rectum.

Next, the user continues to sit on the toilet seat 2 for at least 60-300 seconds, and defecates several times before he/she desire to defecate disappears and then stands up. In this way, a process for emptying the rectum is completed.

Embodiment 3

The outlet diameter of the rectum flushing nozzle 12a is 2.5 mm.

With the temperature of the water flow controlled at 41° C., the user is seated on the toilet seat 2, so that the rectum flushing nozzle 12a of the nozzle head 11 of the toilet is located beneath the user's anus. The distance between the rectum flushing nozzle 12a and the user's anus is kept at 100 mm.

After the relative pressure is set to 0.075 MPa by the water-pressure setting means 60, the water pump 51 is started for supplying water, and a linear water flow is sprayed to the user's anus from the rectum flushing nozzle 12a. The flushing means 4 is controlled to extend out and is moved back or forth so that the linear water flow sprayed from the nozzle 12a aims at the anus and enters into the rectum through the anus.

Then when the user feels that the anus is relaxed, the relative water pressure for spraying the linear water flow is increased to 0.14 MPa. The water flow is continuously sprayed under this relative water pressure to enter into the rectum until the user has a desire to defecate. After the water flow under the relative pressure of 0.14 MPa is sprayed for 20 seconds, the water pump 51 is stopped so that the nozzle 12a stops spraying water and the user defecates.

After that, the user continues be seated on the toilet seat for 60-300 seconds and defecates several times so that his/her desire to defecate disappears and he/she stands up. In this way, a process for emptying the rectum is completed.

It could be understood that although the method of the present invention embodies a method for flushing a rectum by using a nozzle head 11 with the rectum flushing nozzle 12a, the buttock flushing nozzle 12b and the pubic area flushing nozzle 12c, a nozzle head which contains only the rectum flushing nozzle 12a, or only the rectum flushing nozzle 12a and the buttock flushing nozzle 12b, or only the enema nozzle 12a and the pubic area flushing nozzle 12c, also fall in the protection scope of the method of the present invention. Any modifications or changes made by the skilled in the art without departing from the concept of the present invention should fall in the protection scope of the present invention.

What is claimed is:

1. A method for emptying a rectum by using a retractable human body flushing means of an electronic sanitary appliance which is arranged on a toilet, the electronic sanitary appliance comprises a main body unit, a toilet seat, and a retractable human body flushing means which extends out to locate underneath of the toilet seat and retracts into the main body unit, the human body flushing means comprising a nozzle head with one rectum flushing nozzle for producing one first straight aiming water column for aiming at an anus of a user and for producing one second straight rectum-entering water column for entering into the rectum for a distance, the method comprising:
1) extending out the rectum flushing nozzle of the nozzle head so that it locates underneath of the anus of a user who is seated on the toilet seat;
2) generating the first straight aiming water column by the rectum flushing nozzle, spraying it to the anus, and adjusting the position between the rectum flushing nozzle and the user's anus so that the first straight aiming water column aims at the anus and the first straight aiming water column aligns with the anus;
3) then spraying the anus with a straight water column, which does not enter into the anus and is formed by increasing the pressure of the first straight aiming water column, so as to relax the muscle of the anus;
4) spraying the anus with the second straight rectum-entering water column from the rectum flushing nozzle which is formed by increasing relative water-pressure of the straight water column in step 3), so that the second straight rectum-entering water column passes through the anus in a straight line and enters into the rectum;
5) spraying continuously the second straight rectum-entering water column and stopping spray of the second straight water column when the user has a desire to defecate, so that the user evacuates substance in the rectum, wherein the rectum flushing nozzle is provided with a bore having a conical shape so that its diameter gradually reduces from its inlet diameter to its outlet diameter.

2. The method for emptying the rectum by using an electronic sanitary appliance according to claim 1, wherein the first straight aiming water column is sprayed under a relative pressure in the range from 0.03 MPa to 0.055 MPa, and the second straight rectum-entering water column is sprayed under a relative pressure in the range from 0.07 MPa to 0.14 MPa.

3. The method for emptying the rectum by using an electronic sanitary appliance according to claim 2, wherein the second straight rectum-entering water column is sprayed under a relative pressure which increases in a stepwise way.

4. The method for emptying the rectum by using an electronic sanitary appliance according to claim 3, wherein the relative pressure difference of the second straight rectum-entering water column between adjacent two relative pressures is in the range from 0.01 MPa to 0.06 MPa.

5. The method for emptying the rectum by using an electronic sanitary appliance according to claim 1, wherein in step 5), after evacuating substance in the rectum, the user continues to sit on the toilet seat for a certain time and evacuates at least one time.

6. The method for emptying the rectum by using an electronic sanitary appliance according to claim 1, wherein the distance between the rectum flushing nozzle and the anus is in the range from 5 mm to 150 mm, the outlet diameter of the rectum flushing nozzle is in the range from 0.8 mm to 2.5 mm, and a ratio between the outlet diameter and the length of the nozzle bore is in the range of 1:3 to 1:20.

7. The method for emptying the rectum by using an electronic sanitary appliance according to claim 1, wherein the temperature of the first straight aiming water column and the second straight rectum-entering water column is in the range from 25° C. to 41° C.

8. A method for emptying a rectum by using a retractable human body flushing means of an electronic sanitary appliance, wherein the electronic sanitary appliance comprises a main body unit, a toilet seat, and a retractable human body flushing means which extends out to locate below the toilet seat and retracts into the main body unit, the human body flushing means comprising a nozzle head with one rectum flushing nozzle for producing one first straight aiming water column for aiming at an anus of a user and for producing one second straight rectum-entering water column for entering into the rectum for a distance, wherein the method comprises:

1) extending out the rectum flushing nozzle of the nozzle head so that it locates below the anus of a user sitting on the toilet seat;

2) generating the first straight aiming water column by the rectum flushing nozzle, spraying it to the anus, and adjusting the position between the rectum flushing nozzle and the user's anus so that the first straight aiming water column aims at the anus and the first straight aiming water column aligns with the anus;

3) then spraying the anus with a straight water column, which does not enter into the anus and is formed by increasing the pressure of the first straight aiming water column, so as to relax the muscle of the anus;

4) spraying the anus with the second straight rectum-entering water column from the rectum flushing nozzle which is formed by increasing relative water-pressure of the straight water column in step 3), so that the second straight rectum-entering water column passes through the anus in a straight line and enters into the rectum;

5) spraying the anus with the second straight rectum-entering water column and stopping spray of the second straight water column when the user has a desire to defecate, so that the user evacuates substance in the rectum, wherein the rectum flushing nozzle is provided with a bore having a conical shape so that its diameter gradually reduces from its inlet diameter to its outlet diameter.

9. The method for emptying the rectum by using an electronic sanitary appliance according to claim 8, wherein the first straight aiming water column is sprayed under a relative pressure in the range from 0.03 MPa to 0.055 MPa, and the second straight rectum-entering water column is sprayed under a relative pressure in the range from 0.07 MPa to 0.14 MPa.

10. The method for emptying the rectum by using an electronic sanitary appliance according to claim 8, wherein the distance between the rectum flushing nozzle and the anus is in the range from 5 mm to 150 mm, the outlet diameter of the rectum flushing nozzle is in the range from 0.8 mm to 2.5 mm, and a ratio between the outlet diameter and length of the nozzle bore is in the range of 1:3-1:20.

11. The method for emptying the rectum by using an electronic sanitary appliance according to claim 8, wherein the second straight rectum-entering water column of step 4) is sprayed for at least 2 seconds.

12. The method for emptying the rectum by using an electronic sanitary appliance according to claim 11, wherein the second straight rectum-entering water column of step 4) is sprayed for between 30 seconds and 70 seconds.

* * * * *